US008663087B2

(12) United States Patent
Kolar

(10) Patent No.: US 8,663,087 B2
(45) Date of Patent: Mar. 4, 2014

(54) COMPACT EXPANDABLE EROGENIC STIMULATION DEVICE FOR MEN

(76) Inventor: Paul D. Kolar, St. Charles, MO (US)

( * ) Notice: Subject to any disclaimer, the term of this patent is extended or adjusted under 35 U.S.C. 154(b) by 0 days.

(21) Appl. No.: 13/876,410

(22) PCT Filed: Aug. 31, 2012

(86) PCT No.: PCT/US2012/053555

§ 371 (c)(1), (2), (4) Date: Mar. 27, 2013

(87) PCT Pub. No.: WO2013/033660

PCT Pub. Date: Mar. 7, 2013

(65) Prior Publication Data

US 2013/0184521 A1 Jul. 18, 2013

Related U.S. Application Data

(60) Provisional application No. 61/529,906, filed on Aug. 31, 2011.

(51) Int. Cl.
*A61F 5/00* (2006.01)

(52) U.S. Cl.
USPC .......... 600/38

(58) Field of Classification Search
USPC .......... 600/38–41; 128/830–844, 918; 604/346–349
See application file for complete search history.

(56) References Cited

U.S. PATENT DOCUMENTS

| | | | | |
|---|---|---|---|---|
| 5,458,559 A | | 10/1995 | Gauntlett | |
| 5,466,235 A | | 11/1995 | Shubin, Sr. | |
| 5,782,818 A | * | 7/1998 | Shubin | 604/349 |
| 5,807,360 A | | 9/1998 | Shubin | |
| 5,823,939 A | | 10/1998 | Tsagarakis | |
| 5,836,865 A | | 11/1998 | Ritchie et al. | |
| 6,113,532 A | | 9/2000 | Yap | |
| 8,349,417 B2 | | 1/2013 | Heffernan | |
| 2006/0047182 A1 | | 3/2006 | Cochran | |

* cited by examiner

*Primary Examiner* — John Lacyk
(74) *Attorney, Agent, or Firm* — Matthews Edwards LLC

(57) ABSTRACT

An erogenic stimulation device for men having a compact state for inconspicuous storage when not in use which expands to an approximate size and shape of a female pelvic region when filled with warm water, the cooperation of warm water with elastomeric interior and exterior elements provides a more natural sensation of warmth, pressure, and responsive motion for the user, the device including contours simulating the structural features of the pelvic region and buttocks and an anatomically correct depiction of female genitalia including vulva and vaginal opening.

29 Claims, 10 Drawing Sheets

COMPACT EXPANDABLE EROGENIC STIMULATION DEVICE FOR MEN

This application is submitted under 35 U.S.C. 371 claiming priority to PCT/US2012/53555, filed Aug. 31, 2012, which application claims the benefit of U.S. Provisional Application No. 61/529,906, filed Aug. 31, 2011.

TECHNICAL FIELD

The present invention relates to sexual stimulation devices, and more specifically to an erogenic stimulation device for men having a compact state for storage which expands to approximate a female pelvic region and buttocks when filled with warm water, the cooperation of warm water with interior and exterior elastomeric elements provides a more natural interior sensation, natural body temperature, and responsive dynamic motion.

BACKGROUND ART

The disclosure of U.S. Provisional Application No. 61/529,906, filed Aug. 31, 2011, is hereby incorporated herein in its entirety by reference.

Marital or sexual aids (commonly referred to as "sex toys") have been known and used throughout the centuries by both men and women. Generally, sex toys for men are compact, relatively static, and merely provide an approximation of a vaginal tract and opening made of an elastomeric material, such as one of many types of rubber or similar material, sometimes with realistic external features, sometimes without.

On drawback of these common devices is the attempt to approximate a correct feeling of tightness about the user's penis and develop friction between the simulated vaginal tract and the user's penis through a narrow vaginal tract and/or opening. However, a successful implementation of this approach requires custom sizing of the vaginal tract and/or opening to optimally suit the size of the individual user's penis.

An undesirable attribute of these common devices the simulated vaginal tract is open at both ends, which when in use creates unnatural and distracting suction noises. In addition, it has been noted that these devices allow leakage of lubricant and/or seminal fluid through the open end.

To provide physical stimulation, these devices are generally held in the user's hand(s) and moved back and forth along the length of the penis, or held stationary and the penis is moved in and out of the device, or a combination of both. The motions available to the user by these common devices are similar to those of manual self-stimulation. While there are some sex toys for men that provide an approximately life sized simulation of a woman's pelvic region, genitalia, and buttocks, these devices are relatively static, and are conspicuous when stored due to their size.

Many of the know devices are unable to provide a natural body temperature thereby detracting from the experience.

Thus, what is sought is an erogenic stimulation device for men, which overcomes one or more of the shortcomings and limitations, set forth above.

SUMMARY OF THE INVENTION

What is disclosed is an erogenic stimulation device for men, which overcomes one or more of the shortcomings and limitations, set forth above.

According to a preferred embodiment of the invention, an erogenic stimulation device for men has a compact state for inconspicuous storage when not in use and an enlarged state when filled with liquid such as warm water. The device includes an exterior element of an elastomeric material disposed about and containing an interior element of an elastomeric material. A cavity is defined between the elements which is associated with an opening of the exterior element. The interior element has an elongate overall shape and includes a first open end, a second open end, and a longitudinally extending passage extending therebetween. The first open end of the interior is disposed in the opening of the exterior element, and the second open end of the interior element is connected to and incorporated into the exterior element so as to be open and accessible through the exterior element to allow insertion of a penis into the passage. A closure element is closable about a portion of the exterior element adjacent to the opening and about the first open end of the interior element. The closure element sealably closes the opening to retain liquid in the cavity and hold the first open end in the closed opening.

When a quantity of the liquid is retained in the cavity under pressure, the liquid exerts an external force against the interior element and an internal force against the exterior element, reducing the passage in size in at least one direction and expanding the exterior element from a compact state to an enlarged state.

When the quantity of the liquid is removed from the cavity, the forces against the interior and exterior elements are removed, and the exterior element reduces in size from the enlarged state to the compact state. Also, when empty, the user may clean the device by running water through the passage between the first and second open ends.

According to a preferred feature of the invention, the exterior element is cooperable with the quantity of the retained liquid to propagate forces imparted by a user against the exterior element of the cavity throughout the cavity, including against the interior element.

According to a feature of the present invention, the exterior element enlarges to an approximate shape of a female pelvic region and buttocks. To create this shape, another preferred feature of the invention varies the thickness of walls of the exterior element to control the shape when enlarged, and yet another preferred feature provides a yoke of flexible ribs to create natural looking contours.

According to yet another preferred feature of the invention, a detail portion comprising simulated female genitalia is disposed on the exterior element at the second open end of the interior element. To maintain a natural look, a flexible, inelastic cord may be disposed within the ribs adjacent to the detail portion configured to limit expansion of a region therearound.

Advantages of the invention include the compact state of the device which is relatively small and inconspicuous to store when not in use, the natural feeling created by warm liquid exerting pressure, rather than tightness, on the user's penis, and elimination of the unnatural sucking noises and leakage of lubricant and/or seminal fluid during use. The forces exerted on the interior element during use provide a closer approximation of the natural pressures exerted on the penis by a woman's vagina during coitus. Warm water provides natural body temperature. Forces applied to the exterior element during use result in reactive forces imparted by movement of the liquid that provide dynamic responsive motion of the device, such as thrusting, rocking, swaying, and bouncing. The combination of natural interior pressure, natural body temperature, and responsive dynamic motion make the device feel alive and real when in use.

DETAILED DESCRIPTION OF THE INVENTION

Figure 1:
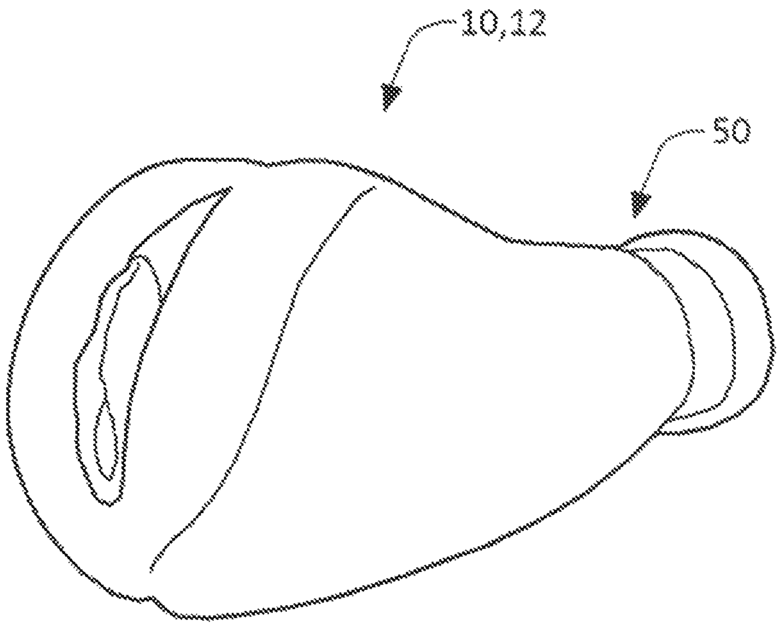
FIG. 1 is a side perspective view of a preferred embodiment of the present invention in a compact state.
Figure 2:
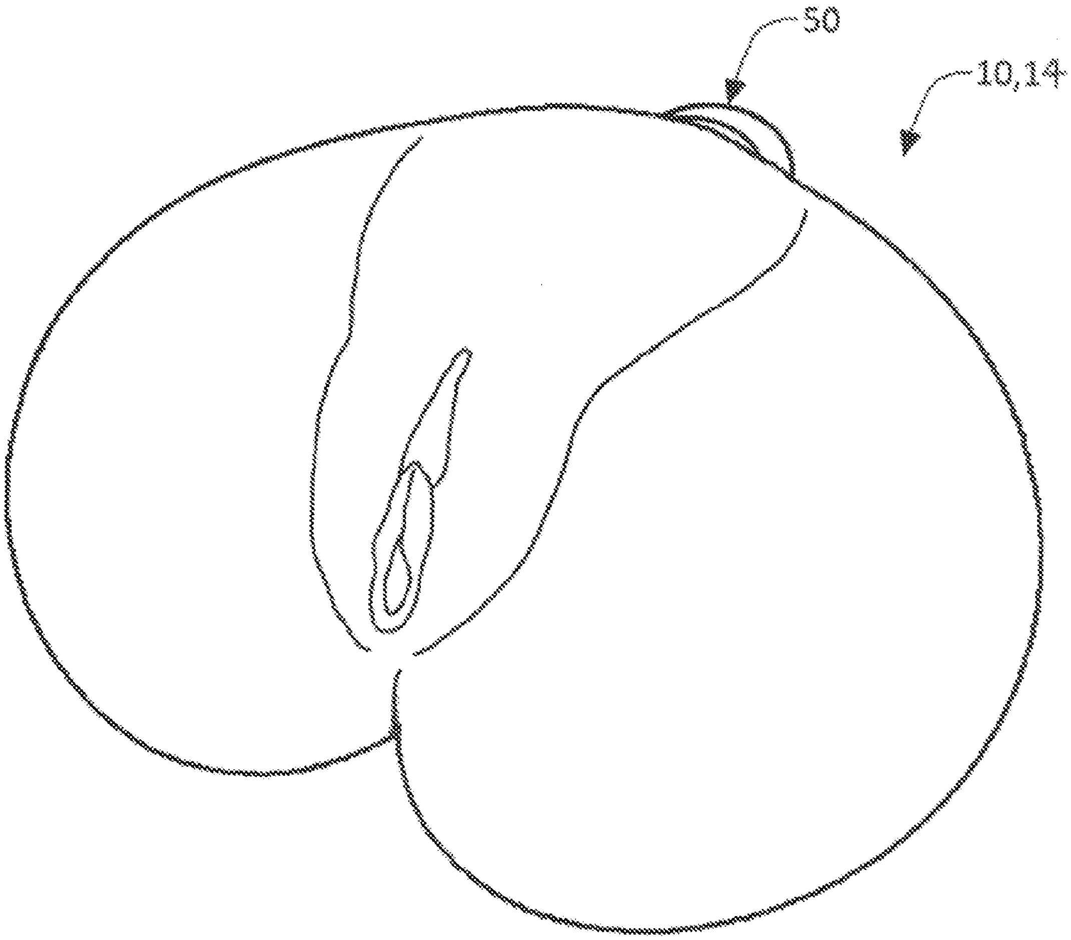
FIG. 2 is a side perspective view of the preferred embodiment of the present invention in an enlarged state.
Figure 3:
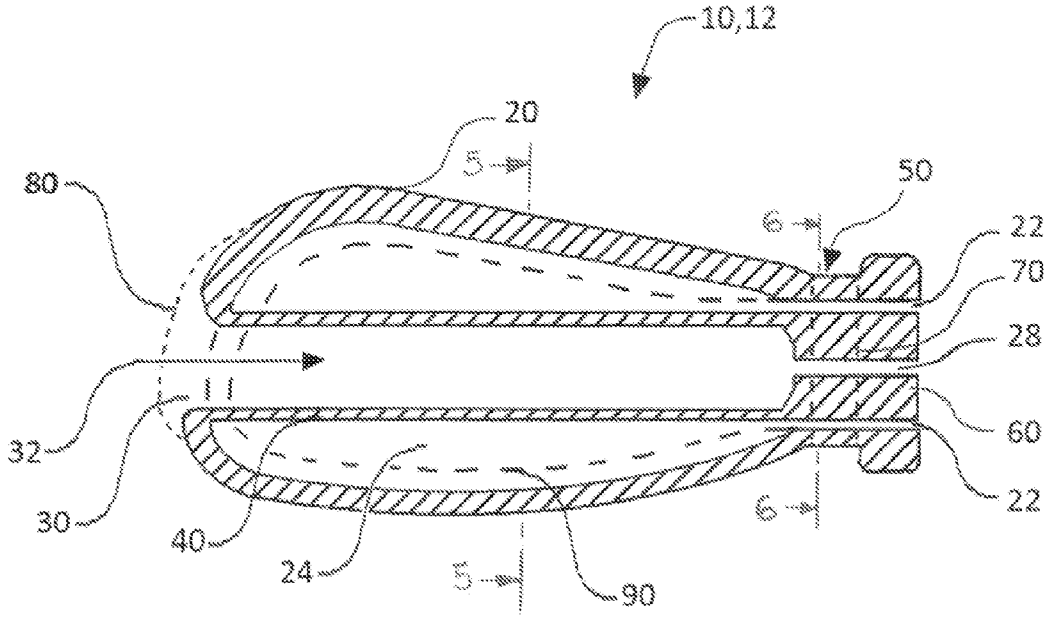
FIG. 3 is a cross section of the preferred embodiment of the present invention taken along line 3-3 of FIG. 5.
Figure 4:
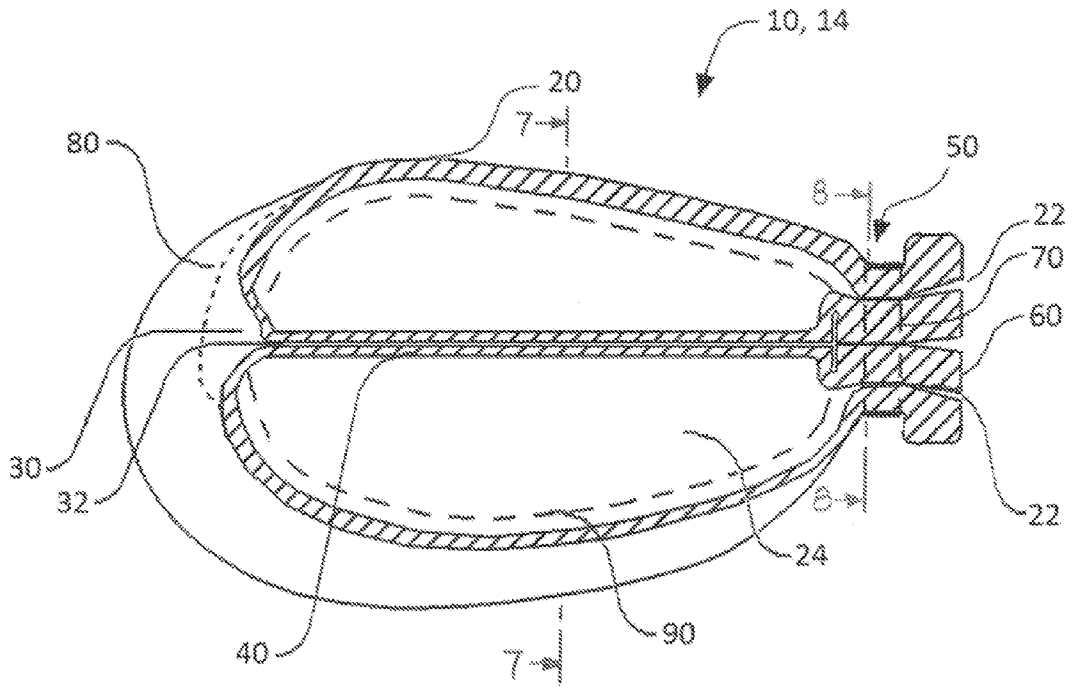
FIG. 4 is a cross section view of the preferred embodiment of the present invention taken along line 4-4 of FIG. 7.
Figure 5:
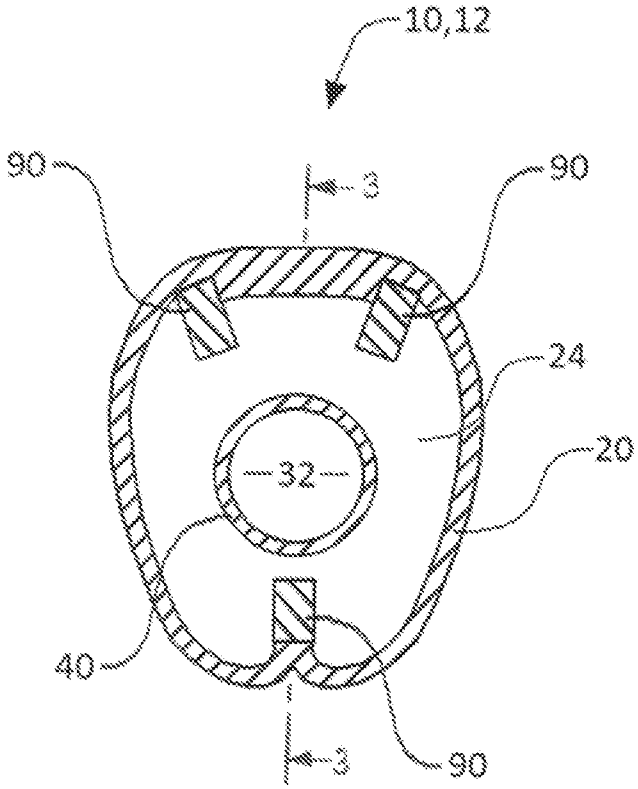
FIG. 5 is a cross section view of the preferred embodiment of the present invention taken along line 5-5 of FIG. 3.

Turning now to the drawings wherein a preferred embodiment of the invention is shown, in FIGS. 1 and 2, a side perspective view of an erogenic stimulation device 10 for men for use in simulated coitus is shown in a compact state 12 and an enlarged state 14, respectively. As seen in FIG. 1, device 10, in compact state 12, may resemble an irregular bottle shape including a bottle neck area 50, although it is contemplated that the shape can vary according to different embodiments. Importantly, compact state 12 is relatively small and inconspicuous for ease of storage when device 10 is not in use.

Turning also to FIGS. 3 through 10, device 10 includes an exterior element 20 of an elastomeric material disposed about and containing an interior element 40 of an elastomeric material. Preferable elastomeric materials include, but are not limited to, rubber, silicone rubber, other suitable elastomers, and the like. A cavity 24 associated with an opening 22 is defined between exterior element 20 and interior element 40. Interior element 40 has an elongate overall shape and includes a first open end 28, a second open end 30, and a longitudinally extending passage 32 extending therebetween. First open end 28 is disposed in opening 22 of exterior element 20 and second open end 30 is connected to and incorporated into exterior element 20 so as to be open and accessible through exterior element 20 to allow insertion of a penis into passage 32.

Figure 8:
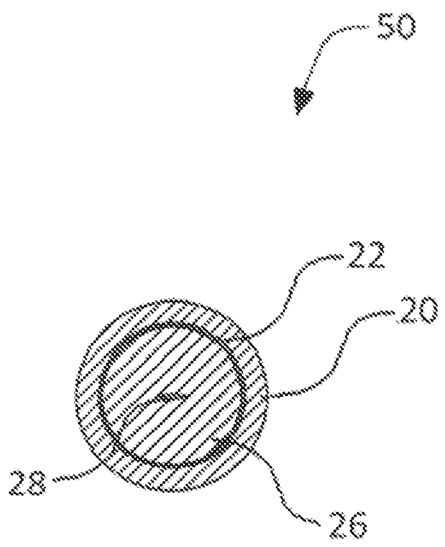
FIG. 8 is a cross section view of the preferred embodiment of the present invention taken along line 8-8 of FIG. 4.
Figure 9:
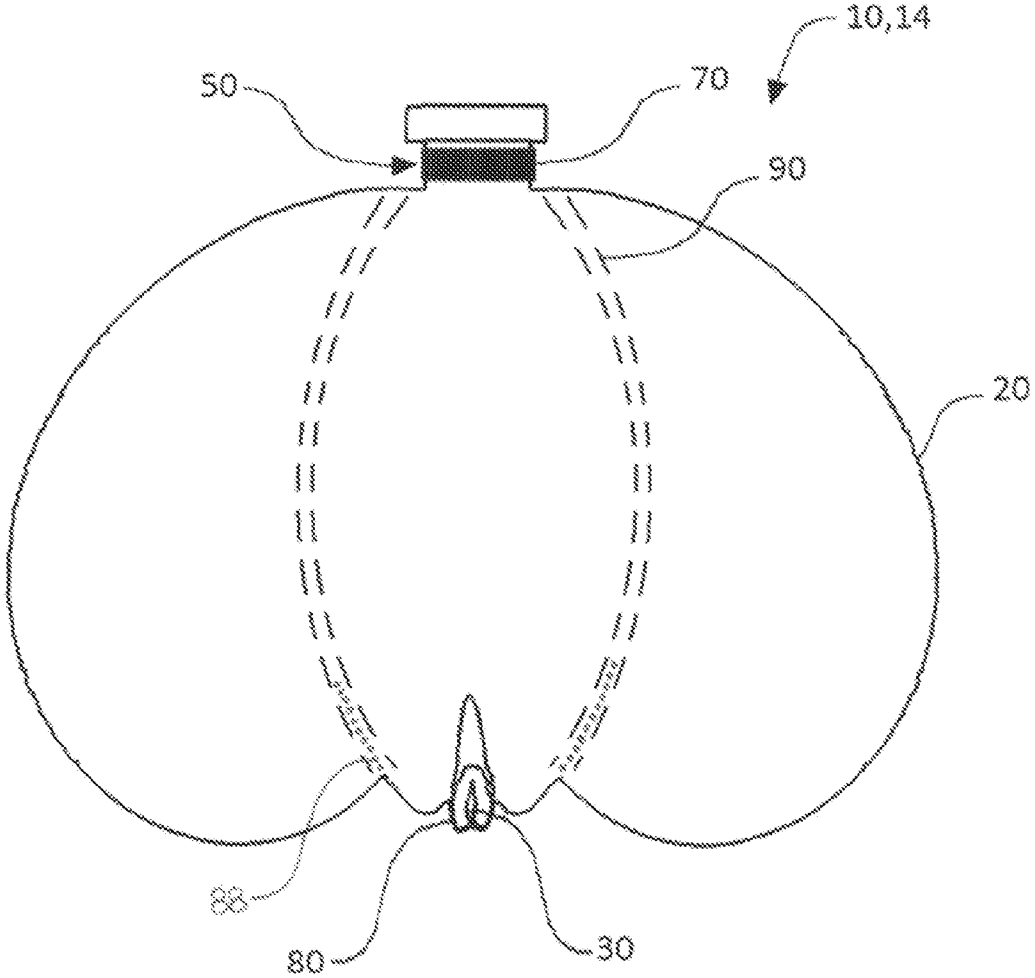
FIG. 9 is a top view of the preferred embodiment of the invention in the enlarged state.
Figure 10:
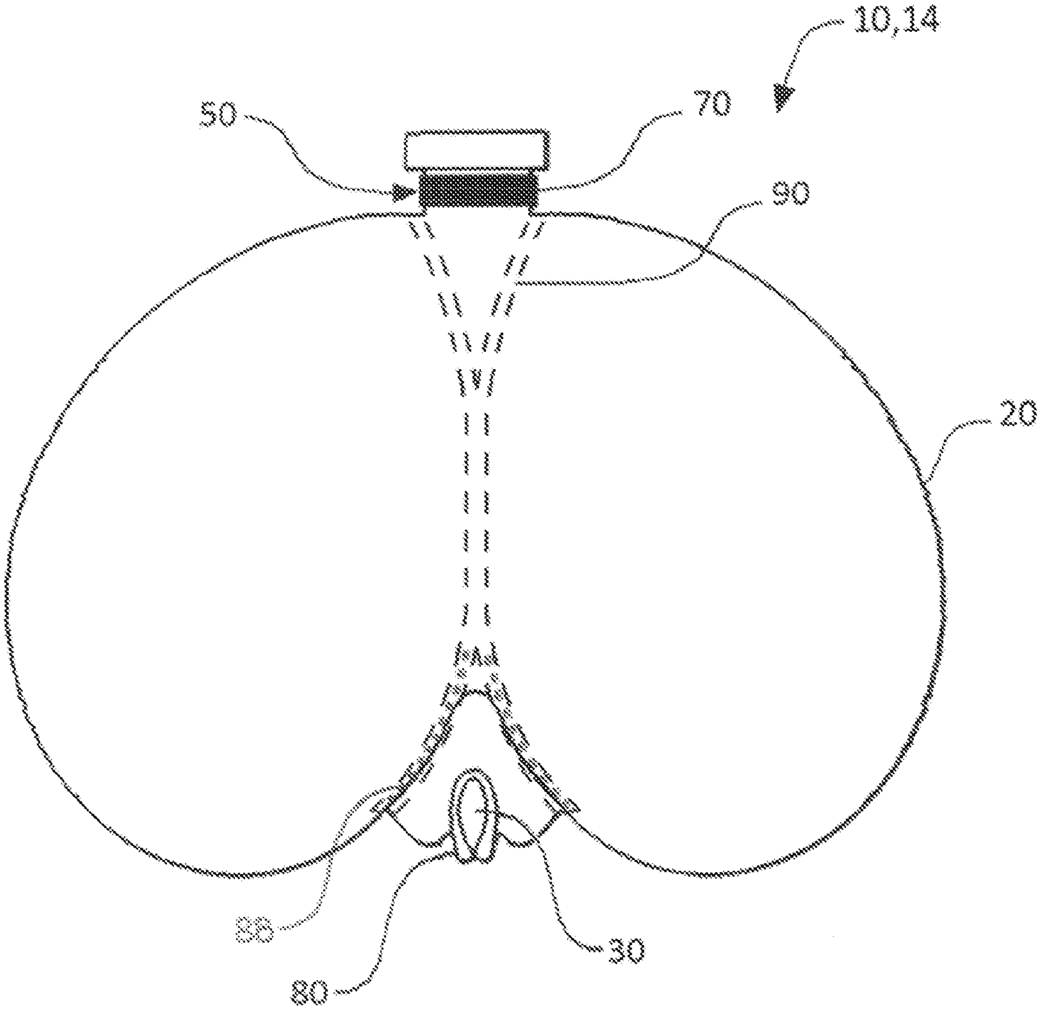
FIG. 10 is a bottom view of the preferred embodiment of the present invention in the enlarged state.

A closure element, shown in FIGS. 9 and 10 as a strap 70, is closable about a portion of exterior element 20 adjacent to opening 22 and about first open end 28 of interior element 40 for sealably closing opening 22 for retaining the liquid in cavity 24 and holding first open end 28 of interior element 40 in the closed opening 22 (FIG. 8). Strap 70 is illustrious of a range of closure elements that are sufficient for constricting bottle neck area 50 and sealably closing first open end 28 and opening 22.

Figure 7:
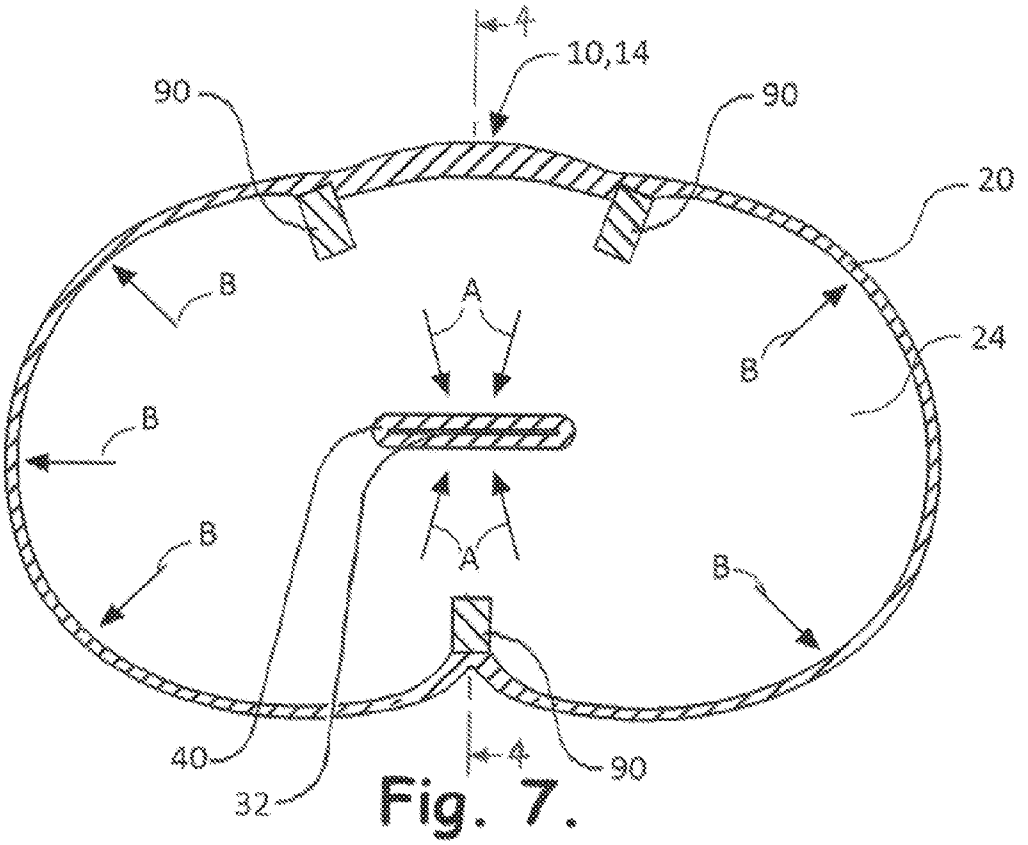
FIG. 7 is a cross section view of the preferred embodiment of the present invention taken along line 7-7 of FIG. 4.

According to a preferred aspect of the invention, retaining a quantity of liquid under pressure, preferably warm water, in cavity 24 exerts an external force, represented by arrows denoted A, against interior element 40 and an internal force, represented by arrows denoted B, against exterior element 20 (FIG. 7). Comparison of FIGS. 3 and 5 to FIGS. 4 and 7, respectively, show second open end 30 and passage 32 is reduced in size in at least one direction and exterior element 20 increases in size from compact state 12 to enlarged state 14.

This aspect of the invention is advantageous because it results in passage 32 simulating a more natural feeling vaginal tract. As explained above, prior art devices rely on narrow passages that fit tightly around the user's penis to approximate the vaginal tract. In other words, the user's penis displaces or stretches the elastic material of the prior art devices on insertion, and the elasticity of the material fighting that deformity causes constriction or tightness around the user's penis. The present invention, however, uses the resiliency of interior element 40, in cooperation with the warm liquid under pressure, to create a custom fit to the user's penis. When entering passage 32, the elasticity of interior element 40 allows the opening of passage 32, rather than constrict around the penis, and the forces exerted by the liquid balance the elasticity to prevent interior element 40 from expanding any more than required by the user. As a result, the user feels the forces exerted by the water, which is a much more natural feeling than the constriction of the elastic material found in the prior art.

As an additional advantage, closing first open end 28 of interior element 40 after the air is evacuated from passage 32 prevents the unnatural sucking noises and leakage of lubricant and/or seminal fluid through first open end 28 which is common in prior art devices.

According to another preferred aspect of the invention, removal of the quantity of the liquid from cavity 24 removes the external force against interior element 40 and the internal force against exterior element 20 reducing exterior element 20 in size from enlarged state 14 to compact state 12 for convenient and inconspicuous storage. Also, when empty, the user may clean device 10 by running water through passage 32 between first and second open ends 28, 30. When in compact state 12, interior element 40 tends to return to its cylindrical shape allowing passage 32 to air dry after cleaning.

According to yet another preferred aspect of the invention, exterior element 20 is cooperable with the quantity of the retained liquid to propagate forces imparted by a user against exterior element 20 of cavity 24 throughout cavity 24, including against interior element 40.

This aspect of the invention is advantageous because as forces exerted on cavity 24 are propagated by the liquid, the user feels the motion of the liquid exerting a responsive pressure against his penis in passage 32, which provides a closer approximation of the natural pressures exerted on the penis by a woman's vagina during coitus. Forces applied to the exterior element during use result in reactive forces imparted by movement of the liquid that provide dynamic responsive motion of device 10, such as thrusting, rocking, swaying, and bouncing. The combination of natural interior pressure, natural body temperature, and responsive dynamic motion make the device feel alive and real when in use.

According to a preferred feature of the invention, in enlarged state 14, exterior element 20 approximates a shape of a female pelvic region and buttocks. To create this shape, another preferred feature of the invention varies the thickness of walls of exterior element 20 to control the shape when enlarged, and yet another preferred feature provides a yoke of flexible ribs 90 to create natural looking contours. Ribs 90 are made of a material less elastic than the material of exterior element 20 and are disposed within exterior element 20 to control expansion thereof when in enlarged state 14. Preferably ribs 90 are fused to exterior element 20 and are configured to contour the shape of exterior element 20 to simulate the pelvic region and buttocks.

According to yet another preferred feature of the invention, a detail portion 80 comprising simulated female genitalia is disposed on exterior element 20 at second open end 30 of interior element 40. To maintain the integrity of detail portion 80 when device 10 is in enlarged state 14, a flexible, inelastic cord 88 disposed within ribs 90 adjacent to detail portion 80 is configured to limit expansion of a region therearound.

Figure 6:
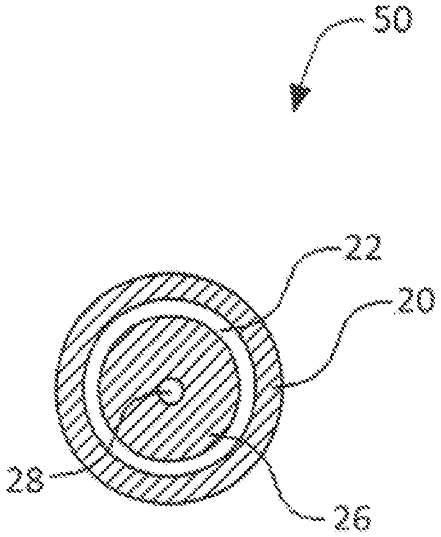
FIG. 6 is a cross section view of the preferred embodiment of the present invention taken along line 6-6 of FIG. 3.

According to yet another preferred aspect of device 10, opening 22 of exterior element 20 is sufficiently larger than first open end 28 for passage of a liquid into and out of cavity 24. This aspect, as seen in FIGS. 6 and 8, facilitates filling cavity 24 with liquid, preferably water, without filling first open end 28. A water faucet can be placed in opening 22 between interior element 40 and exterior element 20 for ease of filling. In addition, the thickness of the material of interior element 40 around first open end 28 provides a plug 26 to aid in sealing opening 22. Plug 26 is created by reducing the inside dimension of interior element 40, thereby thickening the wall of interior element 40 at first open end 28 as interior element 40 passes through bottle neck area 50.

FIGS. 9 and 10 are top and bottom views, respectively, of device 10 in enlarged state 14 illustrating the contours of the pelvic region and buttocks formed by cooperation of exterior element 20 and ribs 90.

In light of all the foregoing, it should thus be apparent to those skilled in the art that there has been shown and described a compact expandable erogenic stimulation device for men. However, it should also be apparent that, within the principles and scope of the invention, many changes are possible and contemplated, including in the details, materials, and arrangements of parts which have been described and illustrated to explain the nature of the invention. Thus, while the foregoing description and discussion addresses certain preferred embodiments or elements of the invention, it should further be understood that concepts of the invention, as based upon the foregoing description and discussion, may be readily incorporated into or employed in other embodiments and constructions without departing from the scope of the invention. Accordingly, the following claims are intended to protect the invention broadly as well as in the specific form shown, and all changes, modifications, variations, and other uses and applications which do not depart from the spirit and scope of the invention are deemed to be covered by the invention, which is limited only by the claims which follow.

What is claimed is:

1. An erogenic device for men for use in simulated coitus, comprising:

an exterior element of an elastomeric material disposed about and containing an interior element of an elastomeric material and defining a cavity therebetween and an opening of the exterior element being in connection with the cavity;

the interior element having an elongate overall shape and including a first open end, a second open end, and a longitudinally extending passage extending therebetween, the first open end being disposed in the opening of the exterior element, and the second open end being connected to and incorporated into the exterior element so as to be open and accessible through the exterior element to allow insertion of a penis into the passage;

the cavity being configured to retain a quantity of liquid for exerting an external force against the interior element and an internal force against the exterior element reducing the passage in size in at least one direction and expanding the exterior element from a compact state to an enlarged state having an approximate shape of a female pelvic region and buttocks;

the exterior element including walls having variations in thickness configured to control the shape of the device in the enlarged state;

flexible ribs less elastic than the exterior element disposed within the exterior element and configured to contour the shape of the device in the enlarged state; and a closure element closable about a portion of the exterior element adjacent to the opening and about the first open end of the interior element for sealably closing the opening for retaining the liquid under pressure in the cavity and holding the first open end in the closed opening.

2. The device of claim 1 wherein removal of the quantity of the liquid from the cavity removes the external force against the interior element and the internal force against the exterior element reducing the exterior element in size from the enlarged state to the compact state.

3. The device of claim 1 wherein responsive dynamic motion is provided in reaction to forces exerted on the device whereby momentum of the retained liquid results in forces on the exterior element producing deformation thereof, and resiliency of the exterior element imparting reverse forces through the liquid creating reactive momentum and movement.

4. The device of claim 1, further comprising a detail portion including simulated female genitalia disposed on the exterior element at the second open end of the interior element.

5. The device of claim 4 further comprising a flexible, inelastic cord disposed within the ribs adjacent to the detail portion configured to further limit expansion of a region therearound.

6. The device of claim 1 including the opening of the exterior element being sufficiently larger than the first open end for passage of a liquid into and out of the cavity, and the interior element having walls being significantly thicker at the first open end disposed in the opening of the exterior element than at the second open end or the passage therebetween, the thicker walls of the first open end forming a plug within the opening.

7. The device of claim 1 wherein the closure element comprises a strap wrapped around the exterior element so as to sealably close the opening of the exterior element and also hold closed the first open end of the interior element disposed within the opening.

8. An erogenic stimulation device for men for use in simulated coitus having a compact state and expandable to an approximate size and shape of a female pelvic region and buttocks, comprising:

an elastomeric interior element defining a generally elongate passage between a first open end and a second open end, and being configured to reduce in size in at least one direction responsive to exertion of an external force thereagainst;

an elastomeric exterior element disposed outwardly of and about the interior element and attached thereto in a manner holding the interior element generally linearly within the exterior element with the first open end of the interior element being aligned towards an opening in the exterior element and the second open end of the interior element being attached to the exterior member such that the second open end is accessible from outside of the exterior element;

the exterior element being elastomeric so as to expand in size from the compact state responsive to exertion of an internal force thereagainst to an enlarged state, and to reduce from the enlarged state to the compact state in absence of exertion of the internal force thereagainst;

the exterior element including walls having variations in thickness configured to control the shape of the device in the enlarged state;

flexible ribs less elastic than the exterior element disposed in the exterior element and configured to contour the shape of the device in the enlarged state to the approximate size and shape of the female pelvic region and buttocks;

the exterior element and the interior element defining a cavity therebetween configured for liquid passage through the opening into and out of the cavity, and closable for retaining the liquid in the cavity, including so as to exert the external force against the interior element and the internal force against the exterior element; and a closing element for closing the opening of the exterior element to retain the liquid therein and for closing the first open end of the interior element.

9. The device of claim 8 wherein responsive dynamic motion is provided in reaction to forces exerted on the device whereby momentum of the retained liquid results in forces on the exterior element producing deformation thereof, and resiliency of the exterior element imparting reverse forces through the liquid creating reactive momentum and movement.

10. The device of claim 8 including the first open end being disposed in the opening of the exterior element and closing the opening of the exterior element closes the first open end of the interior element.

11. The device of claim 8 including the passage being suspended in tension within the exterior element when liquid is retained in the cavity.

12. The device of claim 8 further comprising a detail portion including simulated female genitalia disposed on the exterior element at the second open end of the interior element.

13. The device of claim 12 further comprising a flexible, inelastic cord disposed within the ribs adjacent to the detail portion configured to further limit expansion of a region therearound.

14. The device of claim 8 wherein the interior element includes walls being significantly thicker at the first open end disposed in the opening of the exterior element than at the second open end or the passage therebetween, the thicker walls of the first open end forming a plug within the opening.

15. An erogenic stimulation device for men for use in simulating coitus, comprising:

an interior tubular element of an elastomeric material and an exterior element of an elastomeric material disposed therearound, the exterior element and the interior tubular element being joined together about an opening at a second end of the interior tubular element through an internal cavity of the exterior element to a first end thereof disposed in an opening of the exterior element in connection with the internal cavity;

the cavity being configured to retain a quantity of liquid for exerting an external force against the interior tubular element and an internal force against the exterior element reducing the internal tubular element in size in at least one direction and expanding the exterior element from a compact state to an enlarged state having an approximate shape of a female pelvic region and buttocks;

the exterior element including flexible ribs less elastic than the exterior element disposed in the exterior element and configured to contour the shape of the device in the enlarged state; and the exterior element being closable about the first end of the interior element to sealably enclose the internal cavity at the opening of the exterior element;

whereby responsive dynamic motion is produced in the device through momentum of the retained liquid deforming the exterior element and resiliency of the exterior element imparting responsive momentum.

16. The device of claim 15 wherein removal of the quantity of the liquid from the cavity removes the external force against the interior tubular element and the internal force against the exterior element reducing the exterior element in size from the enlarged state to the compact state.

17. The device of claim 15 wherein the exterior element includes walls having variations in thickness to control the shape of the enlarged state thereof to the approximate shape of a female pelvic region and buttocks.

18. The device of claim 15 further comprising a detail portion including simulated female genitalia disposed on the exterior element at the second open end of the interior element.

19. The device of claim 18 further comprising a flexible, inelastic cord disposed within the ribs adjacent to the detail portion configured to further limit expansion of a region therearound.

20. The device of claim 15 wherein the closure element comprises a strap wrapped around the exterior element so as to sealably close the opening of the exterior element and also hold closed the first end of the interior tubular element disposed within the opening.

21. An erogenic device for men for use in simulated coitus, comprising:

an exterior element of an elastomeric material disposed about and containing an interior element of an elastomeric material and defining a cavity therebetween and an opening of the exterior element being in connection with the cavity;

the interior element having an elongate overall shape and including a first open end, a second open end, and a longitudinally extending passage extending therebetween, the first open end being disposed in the opening of the exterior element, and the second open end being connected to and incorporated into the exterior element so as to be open and accessible through the exterior element to allow insertion of a penis into the passage;

the opening of the exterior element being sufficiently larger than the first open end for passage of a liquid into and out of the cavity;

the interior element having walls being significantly thicker at the first open end disposed in the opening of the exterior element than at the second open end or the passage therebetween, the thicker walls of the first open end forming a plug within the opening; and a closure element closable about a portion of the exterior element adjacent to the opening and about the first open end of the interior element for sealably closing the opening for retaining the liquid under pressure in the cavity and holding the first open end in the closed opening.

22. The device of claim 21 wherein the liquid retained in the cavity exerts an external force against the interior element and an internal force against the exterior element reducing the passage in size in at least one direction and expanding the exterior element from a compact state to an enlarged state.

23. The device of claim 21 further comprising flexible ribs less elastic than the exterior element disposed within the exterior element and configured to contour the device to an approximate shape of a female pelvic region and buttocks when liquid is retained in the cavity.

24. The device of claim 21 further comprising a detail portion including simulated female genitalia disposed on the exterior element at the second open end of the interior element.

25. The device of claim 24 further comprising a flexible, inelastic cord disposed within the ribs adjacent to the detail portion configured to further limit expansion of a region therearound.

26. An erogenic stimulation device for men for use in simulated coitus having a compact state and expandable to an approximate size and shape of a female pelvic region and buttocks, comprising:

an elastomeric interior element defining a generally elongate passage between a first open end and a second open end, and being configured to reduce in size in at least one direction responsive to exertion of an external force thereagainst;

an elastomeric exterior element disposed outwardly of and about the interior element and attached thereto in a manner holding the interior element generally linearly within the exterior element with the first open end of the interior element being aligned towards an opening in the exterior element and the second open end of the interior element being attached to the exterior member such that the second open end is accessible from outside of the exterior element, the exterior element being elastomeric so as to expand in size from the compact state responsive to exertion of an internal force thereagainst and to reduce from the enlarged state to the compact state in absence of exertion of the internal force thereagainst;

the exterior element and the interior element defining a cavity therebetween configured for liquid passage through the opening into and out of the cavity, and closable for retaining the liquid in the cavity, including so as to exert the external force against the interior element and the internal force against the exterior element;

the interior element including walls being significantly thicker at the first open end disposed in the opening of the exterior element than at the second open end or the passage therebetween, the thicker walls of the first open end forming a plug within the opening; and a closing element for closing the opening of the exterior element to retain the liquid therein and for closing the first open end of the interior element.

27. The device of claim 26 further comprising flexible ribs less elastic than the exterior element disposed in the exterior element and configured to contour the shape of the device to the approximate shape of a female pelvic region and buttocks when liquid is retained in the cavity.

28. The device of claim 26 further comprising a detail portion including simulated female genitalia disposed on the exterior element at the second open end of the interior element.

29. The device of claim 28 further comprising a flexible, inelastic cord disposed within the ribs adjacent to the detail portion configured to further limit expansion of a region therearound.

* * * * *